(12) United States Patent
Pelta et al.

(10) Patent No.: US 6,759,551 B1
(45) Date of Patent: Jul. 6, 2004

(54) CHIRAL (S- OR R-METHYLPHENYLGLYCINE) AMINO ACID CRYSTAL AND METHOD FOR PREPARING SAME

(75) Inventors: Isabelle Pelta, Chassieu (FR); Jean-Claude Maret, Decines (FR)

(73) Assignee: Bayer Cropscience S.A. (FR)

( * ) Notice: Subject to any disclaimer, the term of this patent is extended or adjusted under 35 U.S.C. 154(b) by 0 days.

(21) Appl. No.: 10/129,449
(22) PCT Filed: Nov. 3, 2000
(86) PCT No.: PCT/FR00/03064
§ 371 (c)(1), (2), (4) Date: Sep. 11, 2002
(87) PCT Pub. No.: WO01/32603
PCT Pub. Date: May 10, 2001

(51) Int. Cl.[7] ............................................. C07C 229/08
(52) U.S. Cl. ........................................................ 562/443
(58) Field of Search ......................................... 562/443

(56) References Cited

U.S. PATENT DOCUMENTS

| 4,436,910 A | 3/1984 | Kleemann et al. | 546/245 |
| 4,877,908 A | * 10/1989 | Petit et al. | 568/814 |

FOREIGN PATENT DOCUMENTS

| EP | 0629616 | 12/1994 |
| EP | 0673936 | 9/1995 |
| EP | 0915858 | 9/2000 |
| EP | 1076718 | 5/2002 |
| FR | 2499560 | 8/1982 |
| FR | 2693192 | 1/1994 |
| JP | 62103049 | 11/1985 |
| JP | 60224661 | 4/1986 |
| WO | 98/03490 | 1/1998 |
| WO | 9803490 | 1/1998 |
| WO | 0040545 | 7/2000 |

OTHER PUBLICATIONS

Kaptein et al., Tetrahedron: Asymmetry vol. 4, No. 6, pp. 113–116 (1993).*

Patent Abstracts of Japan, vol. 011, No. 317 (C–452), Oct. 15, 1987 & JP 62 103049 A (Mitsui Toatsu Chem Inc), May 13, 1987 cited in the application, abstract.

Patent Abstracts of Japan, vol. 010, No. 094 (C–338), Apr. 11, 1986 & JP 60 224661 A (Mitsui Toatsu Kagaku KK), Nov. 9, 1985, cited in the application, abstract.

D. Obrecht, et al., "44. L–Phenylalanine Cyclohexylamide: A Simple and Convenient Auxilliary for the Synthesis of Optically Pure Alpha, Alpha–Distributed (R)– And (S)–Amino Acids", *Helvetica Chimica ACTA, CH, Verlag Helvetica Chimica ACTA, Basel*, vol. 78, No. 3, 1995, pp. 563–580.

* cited by examiner

*Primary Examiner*—R. Desai
*Assistant Examiner*—Sonya Wright
(74) *Attorney, Agent, or Firm*—Ostrolenk, Faber, Gerb & Soffen, LLP

(57) ABSTRACT

The invention concerns chiral amino acid, is preparation method, and the use of said chiral amino acid as intermediate for the synthesis of chiral organic compounds.

13 Claims, No Drawings

CHIRAL (S- OR R-METHYLPHENYLGLYCINE) AMINO ACID CRYSTAL AND METHOD FOR PREPARING SAME

This application is a 371 of PCT/FR00/03064 filed Nov. 2, 2000.

FIELD OF THE INVENTION

The present invention relates to a chiral α-amino acid in the crystalline form, to its process of preparation and to the use of the said chiral α-amino acid as intermediate in the synthesis of chiral organic compounds.

STATE OF THE ART

Amino acids are compounds which are very widely used in a very large number of fields. In particular, they are becoming increasingly important in the syntheses of compounds for pharmaceutical, veterinary and phytopharmaceutical use. In these fields of human, animal and plant health, there is a constant search for products which are highly active at a low dose. One means of combining these two aspects is to use, in the case of compounds having at least one asymmetric centre, only the optical isomer possessing the desired activity.

It is then necessary to find a simple, economical and efficient means of synthesizing this active optical isomer. This compound generally has a relatively complex chemical structure, so much so that the centre of chirality is introduced during the synthesis, that is to say that it is contributed by a compound with a simpler chemical structure, for example a synthetic intermediate.

Among chiral intermediates which are entirely favoured, chiral amino acids occupy a dominant position in these fields of human, animal and plant health. The problem which is posed is thus to find processes for the synthesis of chiral amino acids which are inexpensive, are readily accessible from an industrial viewpoint and give high yields.

Processes for the preparation of amino acids from hydantoins are known, for example in Patents JP 60224661 and JP 62103049. However, these processes result in racemic amino acids.

Processes for the preparation of chiral amino acids are already known in the literature. They are mainly based on processes for the resolution of racemic mixture by liquid chromatography, resolution by means of alkaloids or resolution by an enzymatic process, such as, for example, in the not yet published French Patent Application No. 98 06339. These various processes for the resolution or for the preparation of chiral compounds exhibit the problem of resulting in products as a mixture in the reaction medium, without it being possible to easily isolate the desired product.

An additional problem is that the chiral amino acids have a degree of purity which is not very satisfactory. This is because the synthesis of chemical compounds developed for uses in human, animal and/or plant health requires synthetic intermediates of very high purity.

Furthermore, it is well known that the purity of such chiral intermediates is difficult to control; in particular, it is relatively difficult to obtain acceptable purities for such syntheses, that is to say purities of greater than 99%.

In point of fact, it is well known that one means for obtaining a high purity consists, for example, in purifying the product which exists in the crystal form. Mention may be made, among these techniques, for example, of recrystallization, which makes it possible, by dissolution of the crystal and then slow recrystallization, to obtain a purity in the region of 100%.

A problem is thus to be able to separate the desired product from the reaction medium, the product having to have a high chemical and enantiomeric purity. In order to obtain this high purity, it is advantageous, for example, to be able to have available the product in the crystalline form. In point of fact, it is well known to a person skilled in the art that to obtain amino acids in the form of crystals from a reaction medium is an operation which is difficult and not described, for example, for the amino acid known as 2-methyl-2-phenylglycine.

General Definition of the Invention

A first object of the invention consists in providing a chiral α-amino acid in the crystalline form, more particularly (S)-(+)-methylphenylglycine (or (S)-(+)-2-phenylalanine) or (R)-(−)-methylphenylglycine (or (R)-(−)-2-phenylalanine) in the crystalline form. A second object of the invention is to provide a process for the preparation of (S)-(+)-methylphenylglycine or of (R)-(−)-methylphenylglycine in the crystalline form from chiral hydantoins. A third object of the present invention is to synthesize chiral organic compounds prepared from (S)-(+)-methylphenylglycine or from (R)-(−)-methylphenylglycine in the crystalline form.

Detailed Definition of the Invention

Thus, a first object of the present invention relates to the (S)-(+)-2-methyl-2-phenylglycine crystal and the (R)-(−)-2-methyl-2-phenylglycine crystal (subsequently named (S)-(+)-methylphenylglycine and (R)-(−)-methylphenylglycine respectively), characterized in that the single crystal is an orthorhombic crystal system, the unit cell parameters of which are a=5.778 Å, =6.692 Å and c=22.127 Å, with a $P2_12_12_1$ space group and possessing four molecules per unit cell.

More particularly, the present invention relates to the (S)-(+)-methylphenylglycine crystal and the (R)-(−)-methylphenylglycine crystal, characterized by the following crystallographic parameters of the single crystal:

| | | |
|---|---|---|
| Crystal system: | orthorhombic; | |
| Unit cell parameters: | a = 5.778 Å | α= 90°; |
| | b = 6.692 Å | β= 90°; |
| | c = 22.127 Å | γ 90°; |
| Asymmetric unit: | 1 molecule; | |
| Space group: | $P2_12_12_1$; | |
| Number of molecules per unit cell: | 4; | |
| Volume of the unit cell: | 855.6 $Å^3$; | |
| Calculated density: | 1.282 $g/cm^3$; | |
| Absorption coefficient $\mu$: | 0.91 $cm^{-1}$ (CuKα). | |

The above parameters are obtained by milling the product and then analysed, in order to obtain an experimental reference diagram with respect to the resolution of the structure: from this powder, a single crystal is synthesized in a suitable solvent or a suitable mixture of solvents, for example water, by very slow evaporation; by means of an X-ray diffraction device specially designed for single crystals, all the diffraction lines are analysed (position, intensity); the crystal parameters are finally obtained using calculating computer programs.

The crystal defined above has in addition the following characteristics of not being a solvate, that is to say that the (S)-(+)-methylphenylglycine or (R)-(−)-methylphenylglycine molecule is not bonded (chemically and/or physically) to a solvent molecule, and of not comprising solvent in the crystal unit cell.

The possibility has thus been discovered of obtaining (S)-(+)-methylphenylglycine (pure enantiomer) or (R)-(−)-methylphenylglycine (pure enantiomer) in the crystalline form, which has in particular the advantage of conferring on this product high chemical and physical stability over time. In particular, (S)-(+)-methylphenylglycine or (R)(−)-methylphenylglycine in the crystalline form exhibits the advantage of not being hygroscopic, which makes possible easy handling, storage and manipulation and which is consequently a major asset when this product is used as starting material in the synthesis of organic compounds.

Thus, another object of the present invention relates to the process for the preparation of (S)-(+)-methylphenylglycine (or of (R)-(−)-methylphenylglycine) in the crystalline form, characterized in that:

(S)-(+)-methylphenylglycine (respectively (R)-(−)-methylphenylglycine) is dissolved, in the free amino acid form or in the salified form, in a pH region of less than approximately 4.5 or greater than approximately 9, then the value of the pH is gradually brought, by addition of a base or of an acid respectively, into a region of greater than approximately 4.5 and less than approximately 9.

The value of the pH of the reaction medium, measured at the beginning of the crystallization reaction, will advantageously be either very much less than 4.5 or very much greater than 9, highly advantageously either less than 2 or greater than 12.

In the process described above, the addition of base or of acid has to be carried out to a reaction medium which is completely dissolved, that is to say devoid of any trace of insoluble compound. Thus, in-addition to the fact of beginning the crystallization at highly acidic or highly basic pH values, it may be advantageous to add one or more suitable solvents which make it possible to dissolve (S)-(+)-methylphenylglycine or (R)-(−)-methylphenylglycine in the free amino acid form or in the salified form. Such solvents are the solvents commonly used to dissolve amino acids, for example water and/or methanol and/or ethanol, and the like.

Under the conditions described above, the first crystals appear when the pH reaches values of between approximately 8.5 and 9 or between approximately 4.5 and 5 pH. These first crystals generally appear without it being necessary to initiate the crystallization. At this stage of the crystallization, the addition of base or of acid can advantageously be slowed down, indeed even halted, in order to make possible optimum formation, optimum maturing and optimum growth of the crystals, this having a direct influence on the physical and chemical quality (yield, purity) of the crystals obtained.

The crystallization is subsequently carried on with by continuing the addition of acid or of base until a pH value of between approximately 5 and 7, preferably between approximately 5 and 6, is obtained, in order to convert all the amino acid to crystals. The crystallization yield is then optimum.

When the starting reaction medium has a pH value of greater than 9, the acid used in the crystallization reaction described above can be an inorganic or organic acid. Preference will be given to an acid of inorganic type, although an organic acid is also suitable. Mention may be made, as nonlimiting example, among the acids which can be used, of hydrochloric acid or of sulphuric acid.

When the starting reaction medium has a pH value of less than 4.5, the base used in the crystallization reaction described above can be an inorganic or organic base. Preference will be given to a base of inorganic type, although an organic base is also suitable. Mention may be made, as nonlimiting example, among the bases which can be used, of sodium hydroxide or of potassium hydroxide.

During the crystallization, it may be advantageous to add a compound which facilitates the agglomeration of the crystals (for the purpose of better filterability, for example). This compound is advantageously chosen from the range of compounds which are known to facilitate the agglomeration of crystals. These compounds are thus, for example, chosen from aromatic organic compounds (monochlorobenzene, toluene, and the like).

It is possible to further increase the yields, as amount of crystals, by carrying out the crystallization reaction starting from (S)-(+)-methylphenylglycine or (R)-(+)-methylphenylglycine solutions which are highly concentrated in amino acid (free or salified). The crystallization will thus advantageously be carried out starting from solutions with a concentration of amino acid of between 4% and 50% by volume. Concentrations of less than 4% also result in the formation of crystals but the yields will be lower. The upper limit of 50% is given by way of indication but it is clearly understood that concentration values of greater than 50% are also compatible with the formation of the desired crystals.

It may also be advantageous to dissolve (S)-(+)-methylphenylglycine or (R)-(−)-methylphenylglycine in the salified form using a solvent, for example water, which is saturated with salt, for example sodium chloride, sodium sulphate or another salt.

In addition, in order to dissolve the whole of the reaction medium, it may also be advantageous to heat the reaction medium in order to obtain complete solubility before carrying out the crystallization stage. This heating stage is particularly suited when the solvent is saturated with salt. The temperature to which the reaction medium is heated must be sufficient to make possible complete dissolution of the amino acid salt and of all entities present in the medium. The reaction medium is advantageously heated to a temperature of between 50° C. and 100° C., preferably between 65° C. and 85° C.

In the case where the reaction medium, comprising the dissolved amino acid which has to be crystallized, comprises other insoluble entities, it is then possible to add a cosolvent. This cosolvent will have the effect of producing a reaction medium which is devoid of any insoluble material, which is necessary to begin the crystallization reaction. This cosolvent is advantageously chosen from conventional water-miscible solvents, such as, for example, an alcohol, such as methanol or ethanol, or solvents such as dimethylformamide or dimethyl sulphoxide.

When the crystallization reaction is complete, the reaction medium comprising (S)-(+)-methylphenylglycine (or of (R)-(−)-methylphenylglycine) in the suspended crystal form is then filtered according to conventional filtration methods and then the crystals are washed and dried according to conventional techniques known per se. In the case where the crystallization reaction has been carried out under warm conditions, it is then advantageous to carry out the filtration under warm conditions at a substantially equivalent temperature.

The (S)-(+)-methylphenylglycine or the (R)-(−)-methylphenylglycine (free forms or salified forms) which have to be crystallized are themselves obtained according to conventional techniques known to a person skilled in the art which are readily accessible in the literature, in Chemical Abstracts and in electronic databases.

By way of example, the (S)-(+)-methylphenylglycine or (R)-(−)-methylphenylglycine salt can be obtained by hydrolysis of phenylhydantoins, as disclosed in the not yet published patent application No. 9900202, the content of which is included here by reference. Other examples of the preparation of (S)-(+)-methylphenylglycine or of (R)-(−)-methylphenylglycine are those employing asymmetric synthesis, resolution, enrichment by equilibration or enzymatic catalysis reactions, as disclosed, for example, in French Patent Application No. 2 778 671, the content of which is included here by reference. It is clearly understood that the (S)-(+)-methylphenylglycine or the (R)-(−)-methylphenylglycine which can be employed in the process of the present invention can be obtained according to any method known to a person skilled in the art.

The (S)-(+)-methylphenylglycine or the (R)-(−)-methylphenylglycine in the crystalline form as described above finds a very particularly advantageous application as synthetic intermediate in the preparation of chiral active materials of use in particular in therapeutics or in agriculture.

Thus, another object of the present invention relates to the process for the preparation of certain 2-imidazolin-5-ones and 2-imidazoline-5-thiones of formula (A) from (S)-(+)-methylphenylglycine or from (R)-(−)-methylphenylglycine obtained substantially in the crystal form according to the process of the present invention. The compounds of formula (A) which are defined below are of use in particular as plant-protection products and are disclosed in particular in Patent Application EP-A-0 629 616.

These compounds correspond to the general formula (A):

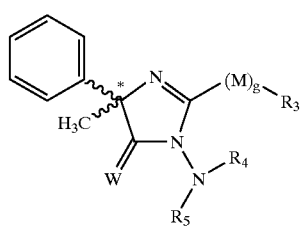

(A)

in which:
W represents an oxygen or sulphur atom or an S=O group;
M represents an oxygen or sulphur atom or a $CH_2$ radical which is optionally halogenated;
p is an integer equal to 0 or 1;
$R_3$ represents:
  a hydrogen or an optionally halogenated $C_1$–$C_2$ alkyl radical, when p is equal to 0 or (M)p is a $CH_2$ radical,
  an optionally halogenated $C_1$–$C_2$ alkyl radical, when (M), represents an oxygen or sulphur atom;
$R_4$ represents:
  the hydrogen atom, or
  an alkyl radical comprising from 1 to 6 carbon atoms, or
  an alkoxyalkyl, alkylthioalkyl, haloalkyl, cyanoalkyl, thiocyanatoalkyl, alkenyl or alkynyl radical comprising from 2 to 6 carbon atoms, or
  a dialkylaminoalkyl, alkoxycarbonylalkyl or N-alkylcarbamoylalkyl comprising from 3 to 6 carbon atoms, or
  an N,N-dialkylcarbamoylalkyl radical comprising from 4 to 8 carbon atoms, or
  an aryl radical, comprising phenyl, naphthyl, thienyl, furyl, pyridyl, pyrimidyl, pyridazinyl, pyrazinyl, benzothienyl, benzofuryl, quinolinyl, isoquinolinyl or methylenedioxyphenyl optionally substituted by 1 to 3 groups chosen from $R_6$, or
  an arylalkyl, aryloxyalkyl, arylthioalkyl or arylsulphonylalkyl radical, the terms aryl and alkyl having the definitions given above;
$R_5$ represents:
  hydrogen or an alkyl, haloalkyl, alkylsulphonyl or haloalkylsulphonyl radical comprising from 1 to 6 carbon atoms, or
  an alkoxyalkyl, alkylthioakyl, acyl, alkenyl, alkynyl, haloacyl, alkoxycarbonyl, haloalkoxycarbonyl, alkoxyalkylsulphonyl or cyanoalkylsulphonyl radical comprising from 2 to 6 carbon atoms, or
  an alkoxyalkoxycarbonyl, alkylthioalkoxycarbonyl or cyanoalkoxycarbonyl radical comprising from 3 to 6 carbon atoms, or
  the formyl radical or a cycloalkyl, alkoxyacyl, alkylthioacyl, cyanoacyl, alkenylcarbonyl or alkynylcarbonyl radical comprising from 3 to 6 carbon atoms, or
  a cycloalkylcarbonyl radical comprising from 4 to 8 carbon atoms, or
  a phenyl, arylalkylcarbonyl, in particular phenylacetyl and phenylpropionyl, arylcarbonyl, in particular benzoyl, optionally substituted by 1 to 3 groups from k, thienylcarbonyl, firylcarbonyl, pyridylcarbonyl, benzyloxycarbonyl, furfuryloxycarbonyl, tetrahydrofurfuryloxycarbonyl, thienylmethoxycarbonyl, pyridylmethoxycarbonyl, phenoxycarbonyl or phenyithiolcarbonyl radical, the phenyl radical being itself optionally substituted by 1 to 3 groups chosen from $R_6$, alkylthiolcarbonyl, haloalkylthiolcarbonyl, alkoxyalkylthiolcarbonyl, cyanoalkylthiolcarbonyl, benzylthiolcarbonyl, furfurylthiolcarbonyl, tetrahydrofurfurylthiolcarbonyl, thienylmethylthiolcarbonyl, pyridylmethylthiolcarbonyl or arylsulphonyl, or
  a carbamoyl radical optionally mono- or disubstituted by:
    an alkyl or haloalkyl group comprising from 1 to 6 carbon atoms,
    a cycloalkyl, alkeriyl or alkynyl group comprising from 3 to 6 carbon atoms,
    an alkoxyalkyl, alkylthioalkyl or cyanoalkyl group comprising from 2 to 6 carbon atoms, or
    a phenyl optionally substituted by 1 to 3 $R_6$ groups,
  a sulphamoyl group optionally mono- or disubstituted by:
    an alkyl or haloalkyl group comprising from 1 to 6 carbon atoms,
    a cycloalkyl, alkenyl or alkynyl group comprising from 3 to 6 carbon atoms,
    an alkoxyalkyl, alkylthioalkyl or cyanoalkyl group comprising from 2 to 6 carbon atoms, or
    a phenyl optionally substituted by 1 to 3 $R_6$ group groups;
  an alkylthioalkylsulphonyl group comprising from 3 to 8 carbon atoms or a cycloalkylsulphonyl group comprising from 3 to 7 carbon atoms;
$R_4$ and $R_5$, taken together can also form, with the nitrogen atom to which they are attached, a pyrrolidino, piperidino, morpholino or piperazino group optionally substituted by an alkyl radical comprising from 1 to 3 carbon atoms;

$R_6$ represents:
- a halogen atom, or
- an alkyl, haloalkyl, alkoxy, haloalkoxy, alkylthio, haloalkylthio or alkylsulphonyl radical comprising from 1 to 6 carbon atoms, or
- a cycloalkyl, halocycloalkyl, alkenyloxy, alkynyloxy, alkenylthio or alkynylthio radical comprising from 3 to 6 carbon atoms, or
- the nitro or cyano group, or
- an amino radical optionally mono- or disubstituted by an alkyl or acyl radical comprising from 1 to 6 carbon atoms or an alkoxycarbonyl radical comprising from 2 to 6 carbon atoms,
- a phenyl, phenoxy or pyridyloxy radical, these radicals optionally being substituted by 1 to 3 identical or different groups chosen from $R_7$, and $R_7$ represents:
- a halogen atom chosen from fluorine, chlorine, bromine or iodine, or
- an alkyl radical comprising from 1 to 6 carbon atoms, or
- an alkoxy or alkylthio radical comprising from 1 to 6 carbon atoms, or
- a haloalkoxy or haloalkylthio radical comprising from 1 to 6 carbon atoms, or
- a nitrile or nitro radical.

The process for the preparation of the compounds of formula (A) can be represented by the following scheme:

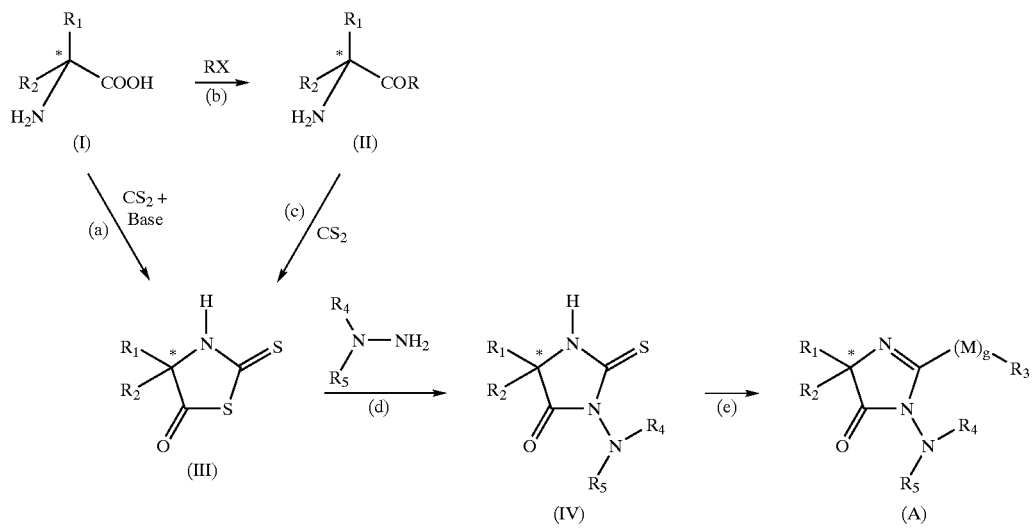

in which scheme the $R_1$ radical represents the methyl radical, the $R_2$ radical represents the phenyl radical, the $R_3$, $R_4$, $R_5$, M, p and W radicals are as defined for the compounds of formula (A), R represents a hydroxyl, alkoxy or benzyloxy radical, the alkoxy radical comprising from 1 to 6 carbon atoms, an amino, alkylamino or dialkylamino radical, an alkylamino radical comprising from 1 to 6 carbon atoms, and X represents a leaving group, such as a halogen atom chosen from chlorine, bromine and iodine or a sulphate or alkylsulphonyloxy or arylsulphonyloxy radical.

In the preceding scheme:
the stages (a), (b), (c) and (d) are disclosed in Patent WO-98/03490, the specific description of which is incorporated here by reference;

the stage (e) is disclosed in Patent EP-A-0 629 616, the specific description of which is incorporated here by reference.

A compound of formula (A) which is very particularly preferred and which can be synthesized from the amino acid in the crystal form according to the present invention is (4S)-4-methyl-2-methylthio-4-phenyl-1-phenylamino-2-imidazolin-5-one, a specific case of the compounds of formula (A) in which the asymmetric carbon atom has the S configuration, W represents the oxygen atom, M represents the sulphur atom, p represents 1, $R_3$ represents the methyl radical, $R_4$ represents the phenyl radical and $R_5$ represents hydrogen.

The purpose of the following example is to illustrate the present invention and it must not under any circumstances be understood as having a limited nature.

EXAMPLE

Formation of (S)-(+)-methylphenylglycine crystals

A basic saline solution comprising the sodium salt of (S)-(+)-methylphenylglycine is brought to approximately 70° C.

The reaction medium is neutralized with sulphuric acid (95%) with slow stirring (300 revolutions/minute). The addition of sulphuric acid is carried out over a period of time of approximately 5 hours, in two parts:

(1) approximately 15% of the total volume of sulphuric acid is added until the value of the pH of the reaction medium changes from 10 to 8.8. The first crystals then appear. The addition of acid is then halted in order to allow the crystals to grow. The reaction medium is maintained for one hour at 72° C. with stirring at a pH of between 8.8 and 8.6;

(2) the remaining amount of sulphuric acid is then added over a period of time of 4 hours until a stable pH with a value of 5 to 6 is obtained for at least half an hour. If the pH has a tendency to fall below 5, a small amount of 20% sodium hydroxide can be added in order to maintain the pH in a region of between 5 and 7.

The suspension of (S)-(+)-methylphenylglycine crystals is then filtered under warm conditions (approximately 70° C.). The crystals obtained are washed once with water (temperature 20 to 25° C.) in order to remove the aqueous-mother liquors and then once with methanol (temperature 20 to 25° C.) in order to remove the water. Finally, the amino acid in the crystalline form is dried under reduced pressure (50 mbar) at 100° C. in order to be stored.

What is claimed is:

1. Process for the preparation of (S)-(+)-2-methyl-2-phenylglycine or of (R)-(−)-2-methyl-2-phenylglycine in the crystalline form, characterized in that:

(S)-(+)-2-methyl-2-phenylglycine (respectively (R)-(−)-2-methyl-2-phenylglycine) is dissolved, in the free amino acid form or in the salified form, in a pH region of less than approximately 4.5 or greater than approximately 9, then the value of the pH is gradually brought, by addition of a base or of an acid respectively, into a region of greater than approximately 4.5 and less than approximately 9.

2. Process according to claim 1, characterized in that the dissolution is carried out in a pH region of less than 2 or greater than 12.

3. Process according to claim 1, characterized in that the amino acid, in the free amino acid form or in the salified form, is dissolved by a solvent.

4. Process according to claim 3, characterized in that the solvent is selected from the group consisting of water, methanol, ethanol, and mixtures thereof.

5. Process according to claim 4, characterized in that the solvent is saturated with salt.

6. Process according to claim 1, characterized in that, after the appearance of the first crystals, the rate of addition of base or of acid is reduced.

7. Process according to claim 1, characterized in that the addition of acid or of base is maintained until a pH value of between approximately 5 and 7, is obtained.

8. Process according to claim 1, characterized in that the acid used is an inorganic acid.

9. Process according to claim 1, characterized in that the base used is an inorganic base.

10. Process according to claim 1, characterized in that a compound which facilitates the agglomeration of the crystals, is added during the crystallization, wherein said compound is selected from the group consisting of monochlorobenzene and toluene.

11. Process according to claim 1, characterized in that the crystallization is carried out starting from solutions with a concentration of amino acid of between 4% and 50% by volume.

12. Process according to claim 1, characterized in that the reaction medium is heated to a temperature of between 50° C. and 100° C.

13. Process according to claim 1, characterized in that a water-miscible cosolvent is added to the reaction medium.

* * * * *